United States Patent
Lee et al.

(10) Patent No.: US 8,742,645 B2
(45) Date of Patent: Jun. 3, 2014

(54) SURFACE ACOUSTIC WAVE SENSOR SYSTEM

(75) Inventors: Hun Joo Lee, Hwaseong-si (KR); Soo Suk Lee, Suwon-si (KR); Yeol Ho Lee, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 250 days.

(21) Appl. No.: 12/705,599

(22) Filed: Feb. 13, 2010

(65) Prior Publication Data

US 2011/0068656 A1    Mar. 24, 2011

(30) Foreign Application Priority Data

Sep. 22, 2009   (KR) .................. 10-2009-0089632

(51) Int. Cl.
*H01L 41/04*   (2006.01)

(52) U.S. Cl.
USPC .............. 310/313 C; 310/313 R; 310/313 A; 310/313 B

(58) Field of Classification Search
USPC ....... 310/313 R, 313 A, 313 B, 313 C, 313 D
See application file for complete search history.

(56) References Cited

U.S. PATENT DOCUMENTS

| | | | | |
|---|---|---|---|---|
| 3,942,140 A | * | 3/1976 | Laker et al. | 333/193 |
| 5,585,684 A | * | 12/1996 | Abe | 310/313 A |
| 5,917,272 A | * | 6/1999 | Clark et al. | 310/343 |
| 6,972,509 B2 | * | 12/2005 | Ikeda et al. | 310/313 D |
| 7,522,020 B2 | * | 4/2009 | Kando | 333/193 |
| 2004/0113215 A1 | * | 6/2004 | Shimada et al. | 257/414 |
| 2007/0046142 A1 | * | 3/2007 | Obara et al. | 310/313 R |
| 2007/0284966 A1 | * | 12/2007 | Kadota et al. | 310/313 R |

FOREIGN PATENT DOCUMENTS

| | | |
|---|---|---|
| JP | 2006-313092 | 11/2006 |
| KR | 10-2001-0072650 | 7/2001 |
| KR | 10-2002-0023029 | 3/2002 |
| KR | 10-2002-0023030 | 3/2002 |
| KR | 10-2003-0088992 | 11/2003 |
| KR | 10-2004-0034721 | 4/2004 |
| KR | 10-2004-0045682 | 6/2004 |
| KR | 10-2004-0079502 | 9/2004 |

* cited by examiner

*Primary Examiner* — Derek Rosenau
*Assistant Examiner* — Bryan Gordon
(74) *Attorney, Agent, or Firm* — Leydig, Voit & Mayer, Ltd.

(57) ABSTRACT

A surface acoustic wave sensor system includes a base substrate, a piezoelectric substrate disposed on the base substrate, inter-digital transducer (IDT) electrodes disposed along a longitudinal direction on the piezoelectric substrate, each IDT electrode including an input inter-digital transducer and an output inter-digital transducer paired with and facing the input inter-digital transducer, each pair of input and output IDTs forming a surface acoustic wave unit sensor with the piezoelectric substrate, and connection electrodes disposed in the base substrate and electrically connected to the surface acoustic wave unit sensors.

13 Claims, 8 Drawing Sheets

SURFACE ACOUSTIC WAVE SENSOR SYSTEM

CROSS-REFERENCE TO RELATED APPLICATION

This application claims priority to Korean Patent Application No. 10-2009-0089632, filed on Sep. 22, 2009, and all the benefits accruing therefrom under 35 U.S.C. §119, the content of which in its entirety is herein incorporated by reference.

BACKGROUND

1. Field

The general inventive concept relates to a surface acoustic wave sensor system and, more particularly, to a surface acoustic wave sensor system having substantially reduced signal interference and noise between unit surface acoustic wave sensors therein.

2. Description of the Related Art

A surface acoustic wave ("SAW") is a mechanical wave (as opposed to an electromagnetic wave, for example,) that is generated from movements of particles by external thermal, mechanical and/or electrical forces. More particularly, a SAW is propagated by vibration energy, most of which is concentrated on a surface of a medium that propagates the SAW. A SAW sensor is a device that senses, e.g., detects, a target material, such as an analyte, using a SAW.

Generally, the SAW sensor is disposed on a substrate made of a piezoelectric material, and includes a receptor that binds to a specific target material on a surface of the SAW sensor. Thus, when a solution, which contains the target material, flows to the SAW sensor, a wavelength is changed by physical, chemical and/or electrical reactions between the target material and the receptor. The resulting change is used to diagnose and monitor the contents of the target material.

The SAW sensor is particularly sensitive to a pressure of a liquid, as well as to viscosity or density of a medium (such as the liquid), and corresponding mass changes on the surface of the SAW sensor. Accordingly, precise control of the liquid is desired to minimize noise, which is a signal change due to factors other than the above-mentioned factors that are used to diagnose and monitor the target material.

In a typical SAW sensor, an oscillation technique or method of applying an output signal, which is emitted from an output inter-digital transducer ("IDT"), to an input IDT of the SAW sensor is used to generate a SAW in an electrode of the SAW sensor. In addition, in the oscillation method, a technique of generating a specific frequency outside the SAW sensor includes applying the specific frequency to the input IDT, and plotting an emitted output signal of the SAW sensor.

The oscillation method has an improved sensitivity over other methods. However, to use the oscillation method, an oscillator is required to be installed in the SAW sensor. The oscillator is generally in contact with and parallel to the SAW sensor.

Since large changes may occur in the SAW sensor, due to pressure gradients needed for fluid flow, for example, a technique and apparatus that reduces an error caused by this pressure is required when the SAW sensor is used.

SUMMARY

The general inventive concept includes a surface acoustic wave ("SAW") sensor system including a plurality of SAW unit sensors.

The general inventive concept also includes a SAW sensor system including a plurality of SAW unit sensors mounted therein, and which substantially reduces signal interference and noise between SAW unit sensors of the plurality thereof.

Provided is a SAW sensor system that includes: a base substrate; a piezoelectric substrate disposed on the base substrate; inter-digital transducer ("IDT") electrodes disposed along a longitudinal direction on the piezoelectric substrate, each IDT electrode including an input IDT and an output IDT paired with and facing the input IDT, each pair of input and output IDTs forming a SAW unit sensor with the piezoelectric substrate; and connection electrodes disposed in the base substrate and electrically connected to the SAW unit sensors.

Also provided is a SAW sensor system wherein the piezoelectric substrates are independently provided to respective surface acoustic wave unit sensors. For example, the SAW sensor system may include: a base substrate; SAW unit sensors disposed on the base substrate, each SAW unit sensor including a piezoelectric substrate and an IDT electrode disposed on the piezoelectric substrate, each IDT electrode including an input IDT and an output IDT paired with and facing the input IDT; and connection electrodes disposed in the base substrate and electrically connected to the surface acoustic wave unit sensors.

The base substrate may include an insulator and, more particularly, the base substrate may be an epoxy resin.

The input and output IDTs each include bar-type electrodes and finger electrodes extending from the bar-type electrodes, and the connection electrodes are electrically connected to the bar-type electrodes.

The input and output IDTs are each formed of one of aluminum and an aluminum alloy, and include an aluminum oxide thin layer formed on a surface thereof.

The connection electrodes are disposed on opposite sides of the piezoelectric substrate (or each of the piezoelectric substrates).

The SAW sensor system may further include oscillators disposed under the base substrate, and each oscillator of the oscillators may be electrically connected to a corresponding SAW unit sensor using the connection electrodes.

The connection electrodes pass through the base substrate substantially perpendicular to a plane defined by the base substrate to connect to the oscillators disposed under the base substrate.

The connection electrodes may be electrically connected to the inter-digital transducer electrodes by conductive wires.

The SAW sensor system may further include cutoffs that prevent a shear horizontal SAW from being transmitted between adjacent SAW unit sensors.

The cutoffs may include grooves formed in the piezoelectric substrate (or substrates) and may be disposed between the SAW unit sensors.

The cutoffs may be barrier walls disposed on the piezoelectric substrate (or substrates) between the SAW unit sensors.

The barrier walls may include a sound wave absorbing material. The sound wave absorbing material may include plastics, waxes and silicon rubbers.

The cutoffs may include guiding layers formed by covering upper surfaces of the SAW unit sensors.

The guiding layers may include a sound wave absorbing material, and each guiding layer may have a thickness from about 0.1 micrometer to about 5 micrometers.

At least one of the SAW unit sensors may be a reaction SAW unit sensor on which a reaction layer is disposed, and the reaction layer may be disposed on the piezoelectric substrate to cover an IDT electrode corresponding to the reaction SAW unit sensor and may include a receptor which binds to a target material.

At least one of the SAW unit sensors may be a reference SAW unit sensor on which a reaction layer is not disposed.

The SAW sensor system analyzes at least two of mass, pressure, density and viscosity of a material by detecting a change in a signal outputted from the output IDTs.

BRIEF DESCRIPTION OF THE DRAWINGS

The above and other aspects and features of the general inventive concept will become more readily apparent by describing in further detail example embodiments thereof with reference to the accompanying drawings, in which.

DETAILED DESCRIPTION

Figure 1:
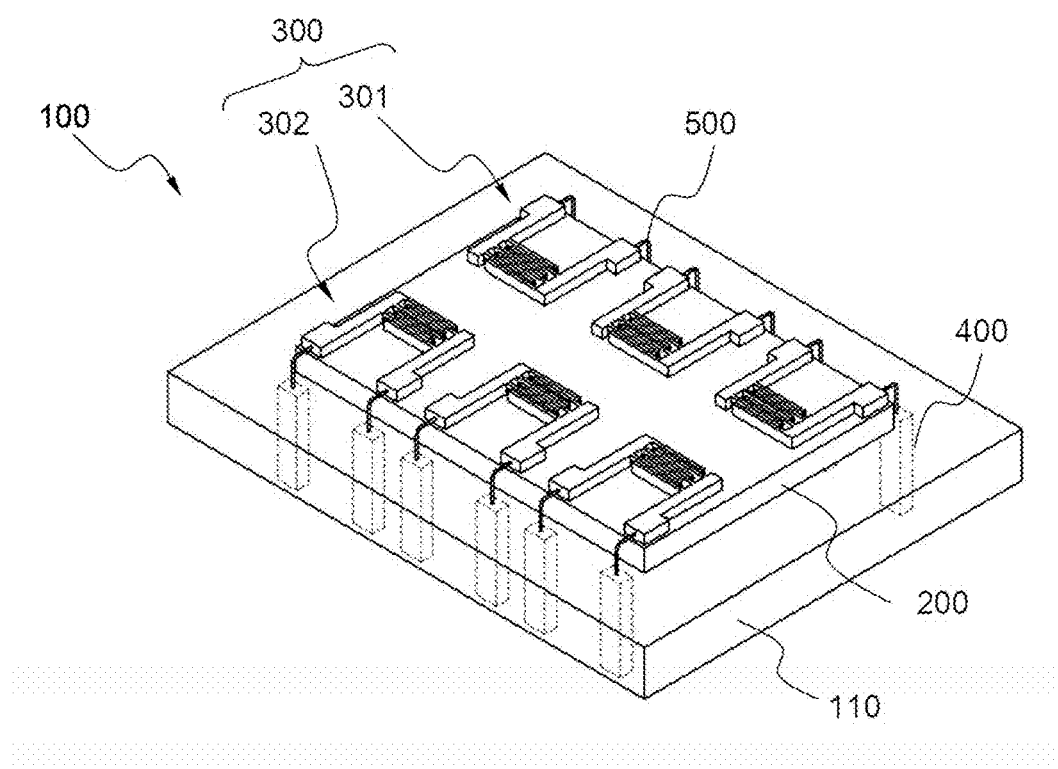
FIG. 1 is a perspective view of a surface acoustic wave ("SAW") sensor system according to an example embodiment.

The general inventive concept now will be described more fully hereinafter with reference to the accompanying drawings, in which various, but not limiting, example embodiments are shown. This invention may, however, be embodied in many different forms, and should not be construed as limited to the example embodiments set forth herein. Rather, these example embodiments are provided so that this disclosure will be thorough and complete, and will fully convey the scope of the general inventive concept to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Example embodiments are described herein with reference to cross section illustrations that are schematic illustrations of idealized example embodiments. As such, variations from the shapes of the illustrations as a result, for example, of manufacturing techniques and/or tolerances, are to be expected. Thus, example embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, example embodiments of the general inventive concept will be described in further detail with reference to the accompanying drawings.

Figure 2:
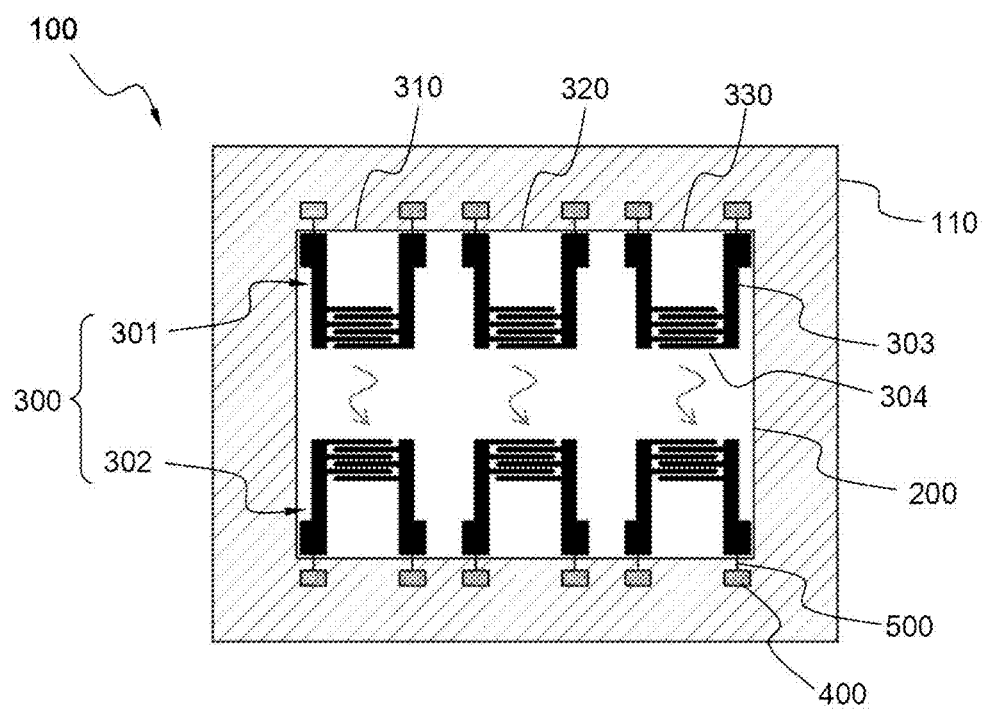
FIG. 2 is a plan view of the SAW sensor system of FIG. 1.
Figure 3:
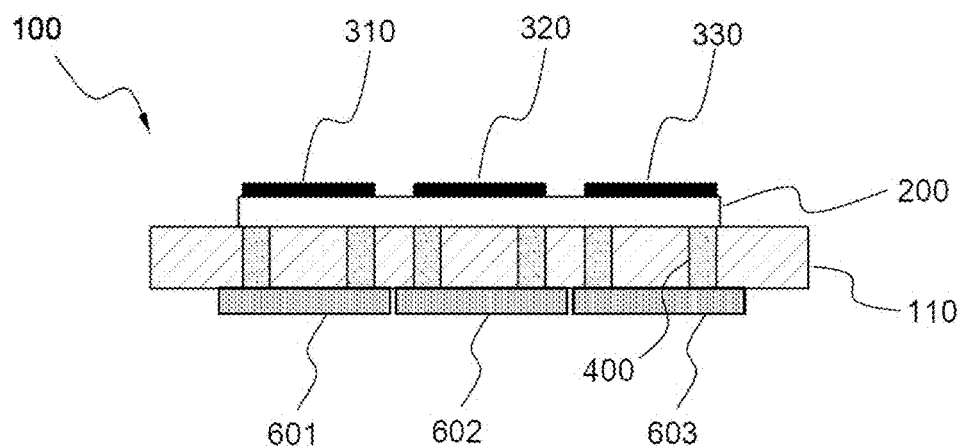
FIG. 3 is a transverse cross-sectional view of the SAW sensor system of FIG. 1.
Figure 4:
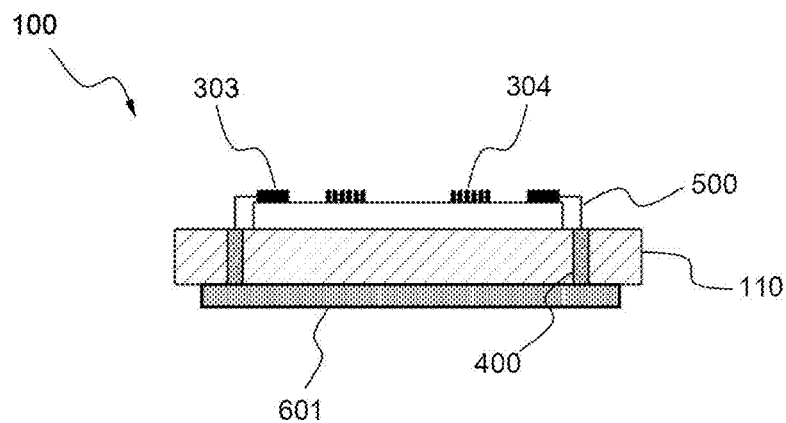
FIG. 4 is a longitudinal cross-sectional view of the SAW sensor system of FIG. 1.

FIGS. 1 to 4 illustrate a surface acoustic wave ("SAW") sensor system according to one or more example embodiments. Specifically, FIG. 1 is a perspective view of a SAW sensor system according to an example embodiment, FIG. 2 is a plan view of the SAW sensor system of FIG. 1, FIG. 3 is a transverse cross-sectional view of the SAW sensor system of FIG. 1, and FIG. 4 is a longitudinal cross-sectional view of the SAW sensor system of FIG. 1. The SAW sensor system will now be described in further detail with reference to FIGS. 1 to 4.

The SAW sensor system 100 includes a base substrate 110, a piezoelectric substrate 200, a plurality of inter-digital transducer ("IDT") electrodes 300, and a plurality of connection electrodes 400.

In an example embodiment, IDT electrodes 300 of the plurality of IDT electrodes 300 are disposed on, e.g., are formed, on the piezoelectric substrate 200 to form a plurality of SAW unit sensors 310, 320 and 330, e.g., a first SAW unit sensor 310, a second SAW unit sensor 320 and a third SAW unit sensor 330, although additional example embodiments are not limited thereto. Since all of the SAW unit sensors 310, 320 and 330 are disposed on a single substrate, e.g., the base substrate 110, the SAW unit sensors 310, 320 and 330 are efficiently mounted on the base substrate 110.

The base substrate 110 may include an insulator, such as an epoxy resin substrate, for example, or a ceramic substrate or other insulating material.

The piezoelectric substrate 200 is formed of a piezoelectric material. The piezoelectric material includes a characteristic in which an electric characteristic thereof changes when a mechanical signal is applied (e.g., a "piezoelectric effect"), and/or a mechanical signal is generated when an electric signal is applied (e.g., an "inverse piezoelectric effect"). Specifically, for example, the piezoelectric material may include, but is not limited to, lithium niobate ($LiNbO_3$), lithium tantalite ($LiTaO_3$), lithium tetraborate ($Li_2B_4O_7$), barium titanate ($BaTiO_3$), lead zirconate ($PbZrO_3$), lead titanate (Pb-$TiO_3$), lead zirconate titanate ("PZT"), zinc oxide (ZnO), gallium arsenide (GaAs), quartz, niobate, or other suitable material.

Each IDT electrode 300 comprises a pair of IDTs 301 and 302. More particularly, the IDT 301 generates the SAW based on an applied signal, and is referred to as an "input IDT 301" or a "transmitter IDT 301." In an example embodiment, the generated SAW is transmitted to the other IDT 302 along a surface of the piezoelectric substrate 200 while being expanded and compressed at a predetermined frequency, and thus is converted into an electric signal by the inverse piezoelectric effect. The other IDT 302 is referred to as an "output IDT 302" or a "receiver IDT 302." The input IDT 301 faces the output IDT 302, as shown in FIGS. 1 and 2.

Referring to FIGS. 2 and 4, each of the IDTs 301 and 302 includes two bar-type electrodes 303 and a plurality of finger electrodes 304 extending from the bar-type electrodes 303 in a comb shape, e.g., the finger electrodes 304 are interdigitated, as shown in FIG. 2. Connection electrodes 400 may be electrically connected to the bar-type electrodes 303.

The IDT electrode 300 is generally formed of a metal thin film of an aluminum (Al) alloy, a copper (Cu) alloy or gold (Au), for example, but is not limited thereto. To prevent the IDT electrode 300 from corroding when the IDT electrode 300 is exposed to air or moisture, for example, a protection layer, such as an anti-oxidation layer, may be disposed on the IDT electrode 300.

In an example embodiment, the IDT electrode 300 may be formed of aluminum or an aluminum alloy, and the anti-oxidation layer may be formed of an aluminum oxide thin film, e.g., an aluminum oxide thin layer. The aluminum alloy may include at least one of Ti, Si, Cr, W, Fe, Ni, Co, Pb, Nb, Ta, Zn and V, in addition to Al, which may be a main component of the aluminum alloy. The anti-oxidation layer may include an artificial aluminum oxide layer or a native aluminum oxide layer, but additional example embodiments are not limited thereto.

The connection electrodes 400 are disposed in the base substrate 110, and are electrically connected with the SAW unit sensors 310, 320 and 330. Thus, the connection electrodes 400 are connected to the input and output IDTs 301 and 302, respectively. As described in greater detail above, the connection electrodes 400 are connected to the IDT electrode 300, constituting the SAW unit sensors 310, 320 and 330, through electric connectors 500, e.g., conductive wires 500. Each electric connector 500 may include a metal wire, a via hole and/or a bonding wire, for example, which allows electrical connection between the abovementioned components.

The connection electrodes 400 may be disposed on opposite sides of the piezoelectric substrate 200. Since the connection electrodes 400 are located on the opposite sides of the piezoelectric substrate 200, a required size of the SAW unit sensors 310, 320 and 330 is substantially reduced. Thus, the connection electrodes 400, located on the opposite sides of the piezoelectric substrate 200, are formed to correspond to ends of the IDT electrodes 300. At least four connection electrodes 400 may be included in one SAW unit sensor, but additional example embodiments are not limited thereto.

As an example, the SAW sensor system 100 may utilize an oscillation mode, and thus may further include oscillators 601, 602 and 603. Specifically, each oscillator 601, 602 and 603 is a circuit that generates a specific frequency of a sine wave signal, for example, and converts DC energy into AC energy. Unlike an amplifier, the oscillator 601, 602 or 603 is configured such that a frequency signal can be detected within a narrow band through only an output port, e.g., without requiring an input port.

The oscillators 601, 602 and 603 may be disposed under the base substrate 110, corresponding to positions of the SAW unit sensors 310, 320 and 330, and may be electrically connected with the SAW unit sensors 310, 320 and 330 through the connection electrodes 400. As illustrated in FIGS. 1 through 4, the connection electrodes 400 may vertically pass through the base substrate 110, e.g., may pass through the base substrate 110 substantially perpendicular to a plane defined by the base substrate 110, and be connected with the oscillators disposed under the base substrate 110.

Figure 5:
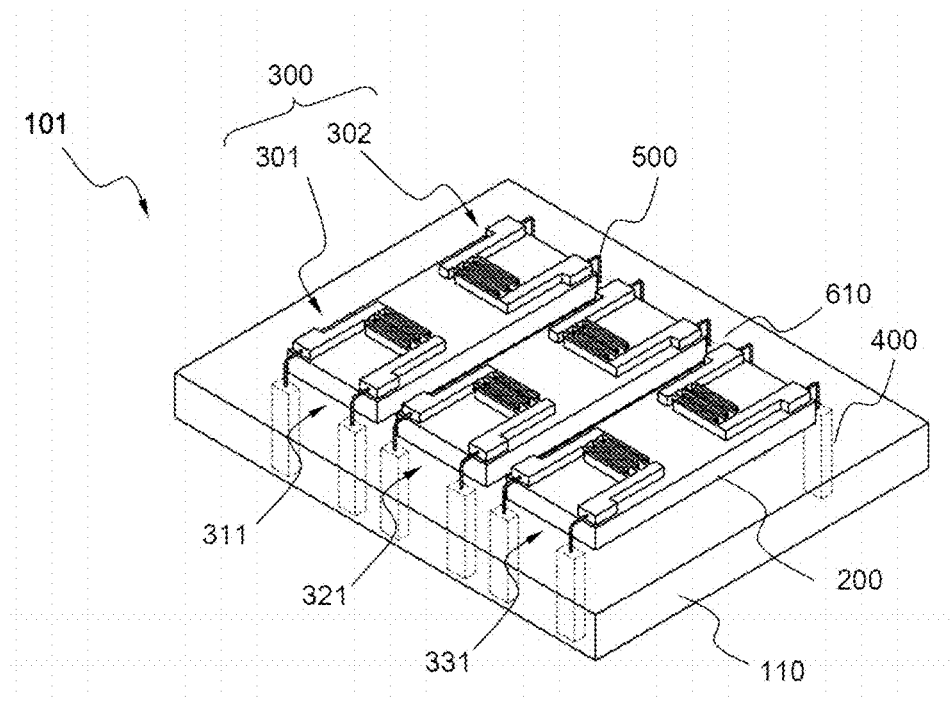
FIG. 5 is a perspective view of a SAW sensor system according to another example embodiment.
Figure 6:
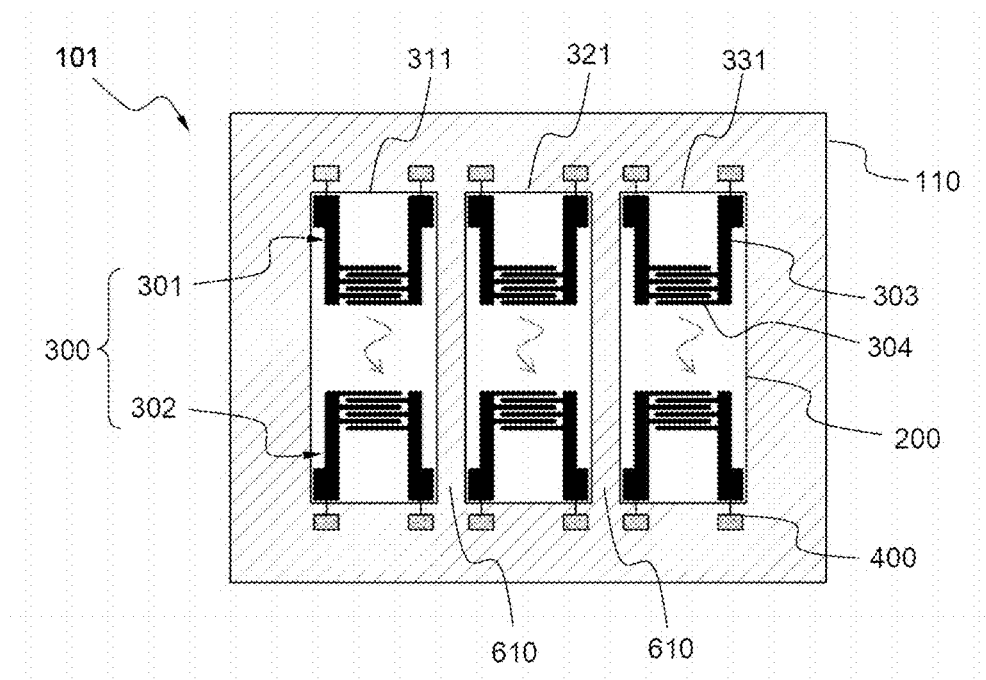
FIG. 6 is a plan view of the SAW sensor system of FIG. 5.
Figure 7:
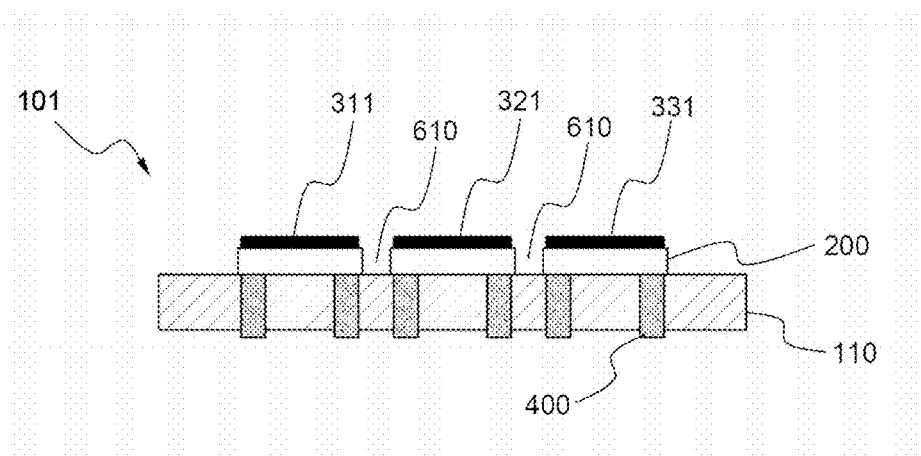
FIG. 7 is a transverse cross-sectional view of the SAW sensor system of FIG. 5.

FIGS. 5 to 7 illustrate a SAW sensor system according to one or more additional example embodiments. Specifically, FIG. 5 is a perspective view of a SAW sensor system according to another example embodiment, FIG. 6 is a plan view of the SAW sensor system of FIG. 5, and FIG. 7 is a transverse cross-sectional view of the SAW sensor system of FIG. 5.

Referring to FIGS. 5 to 7, the SAW sensor system 101 is configured such that piezoelectric substrates 200 are independently provided to respective SAW unit sensors 311, 321 and 331.

The SAW sensor system 101 includes a base substrate 110, a plurality of SAW unit sensors 311, 321 and 331 disposed on the base substrate 110, and a plurality of pairs of connection electrodes 400 disposed in the base substrate 110 and electrically connected with the respective SAW unit sensors 311, 321 and 331.

In an example embodiment, each of the SAW unit sensors 311, 321 and 331 includes a piezoelectric substrate 200, and an IDT electrode 300 disposed on the piezoelectric substrate 200 and including a pair of input and output IDTs 301 and 302, respectively, facing each other, as described in greater detail above with reference to FIGS. 1 to 4.

In the SAW sensor system 101, since the piezoelectric substrates 200 are independently provided to the respective SAW unit sensors 311, 321 and 331, predetermined grooves 610 are formed between the SAW unit sensors 311, 321 and 331. These grooves 610 substantially reduce and/or effectively prevent noise, e.g., a shear horizontal surface acoustic wave ("SH SAW"), from being transmitted to neighboring, e.g., adjacent, SAW unit sensors.

Figure 8:
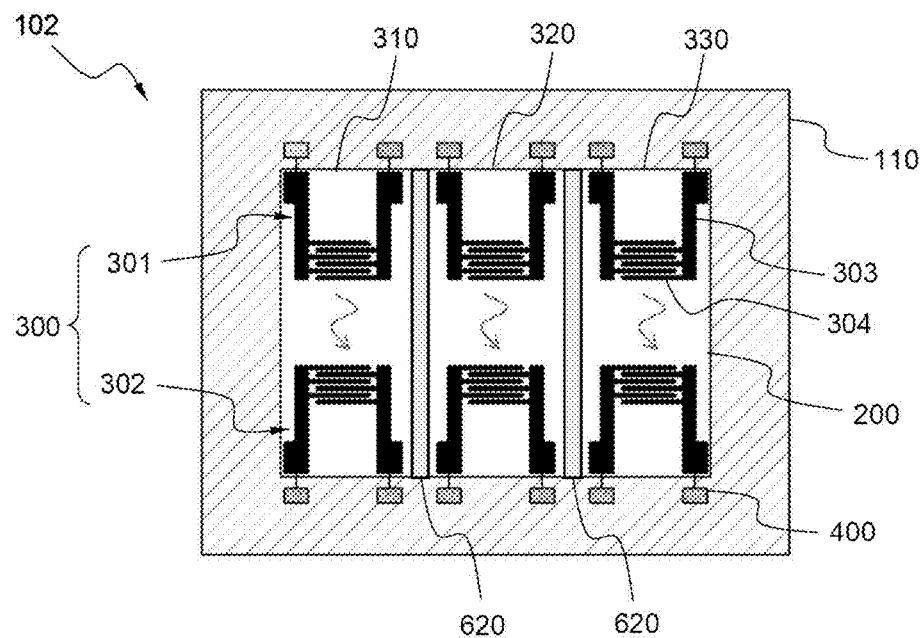
FIG. 8 is a plan view of a SAW sensor system according to still another example embodiment.
Figure 9:
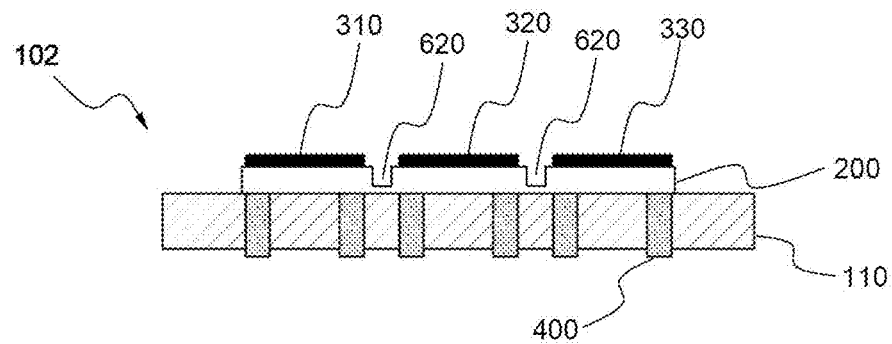
FIG. 9 is a transverse cross-sectional view of the SAW sensor system of FIG. 8.
Figure 10:
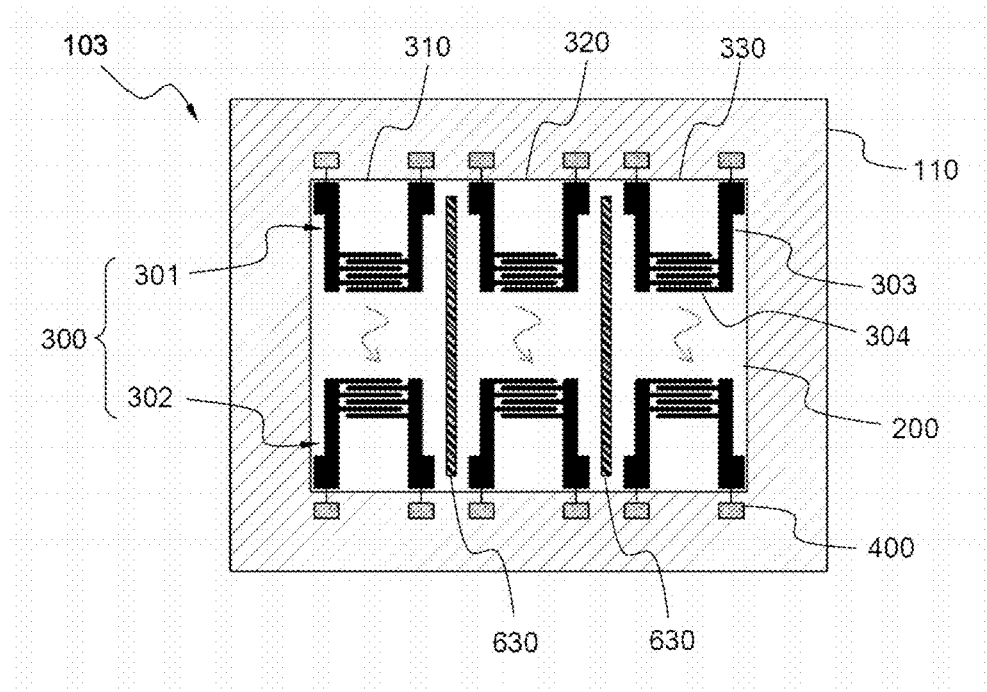
FIG. 10 is a plan view of a SAW sensor system according to yet another example embodiment.
Figure 11:
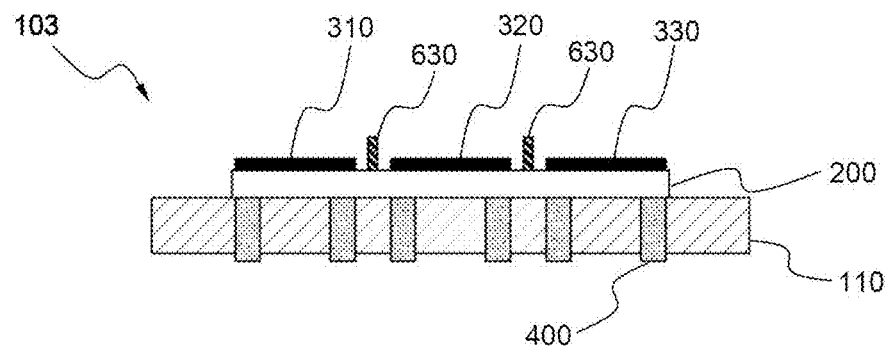
FIG. 11 is a transverse cross-sectional view of the SAW sensor system of FIG. 10.
Figure 12:
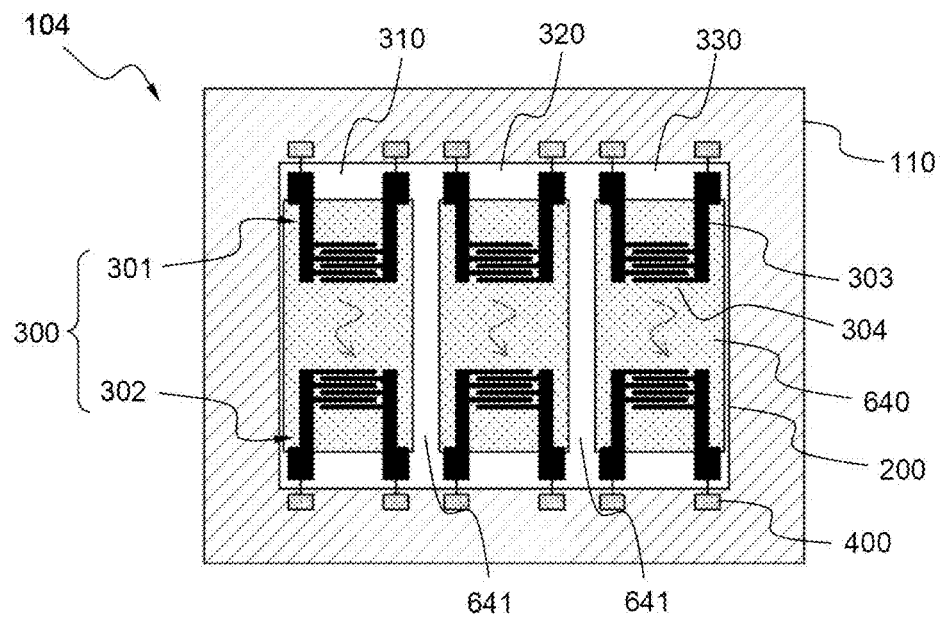
FIG. 12 is a plan view of a SAW sensor system according to another example embodiment.
Figure 13:
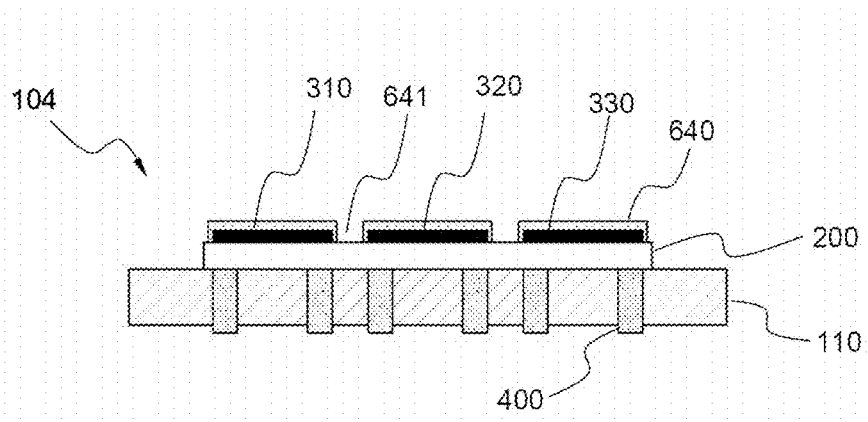
FIG. 13 is a transverse cross-sectional view of the SAW sensor system of FIG. 12.

FIGS. 8 to 13 illustrate a SAW sensor system having cutoffs according to still additional example embodiments. Specifically, FIG. 8 is a plan view of a SAW sensor system according to still another example embodiment, FIG. 9 is a transverse cross-sectional view of the SAW sensor system of FIG. 8, FIG. 10 is a plan view of a SAW sensor system according to yet another example embodiment, FIG. 11 is a transverse cross-sectional view of the SAW sensor system of FIG. 10, FIG. 12 is a plan view of a SAW sensor system according to another example embodiment, and FIG. 13 is a transverse cross-sectional view of the SAW sensor system of FIG. 12.

In one or more example embodiments, each cutoff is a structure that prevents the SH SAW from being transmitted to the neighboring SAW unit sensors, as will now be described in further detail with reference to FIGS. 8 to 13.

Specifically, for example and referring to FIGS. 8 and 9, a SAW sensor system 102 according to an example embodiment includes grooves 620 as the cutoffs between SAW unit sensors 310, 320 and 330 disposed on a base substrate 110.

The grooves 620 are located between the SAW unit sensors 310, 320 and 330, and are disposed in a piezoelectric substrate 200. Thus, the cutoffs effectively prevent the SH SAW, which is transmitted along a surface of the piezoelectric substrate 200, from being transmitted to the neighboring SAW unit sensors.

A method of forming the grooves 620 may include, for example, the grooves 620 being formed by patterning the piezoelectric substrate 200 in intaglio to be exposed between a plurality of IDT electrodes 300. In another example embodiment, the grooves 620 may be formed in the piezoelectric substrate 200, and the IDT electrodes 300 may then be formed, but alternative exemplary embodiments are not limited thereto.

Referring now to FIGS. 10 and 11, another SAW sensor system 103 includes barriers 630, e.g., barrier walls 630, formed as the cutoffs between the SAW unit sensors 310, 320 and 330 and are disposed on a base substrate 110.

The barriers 630 may be formed of a sound wave absorbing material. Thus, the SH SAW, which is transmitted along a surface of the piezoelectric substrate 200, is absorbed by the barriers 630, so that it is not propagated from one SAW unit sensor 310, 320 or 330 to other SAW unit sensors 310, 320 and/or 330. As a result, the neighboring SAW unit sensors are not affected by the SH SAW.

In one example embodiment, for example, the sound wave absorbing material may include a material that has approximately a same impedance as an impedance of the piezoelectric substrate 200, to prevent sound wave energy propagated through piezoelectric substrate 200 from being reflected and/or returned to or towards its original position. This material may include plastic, wax and/or silicon rubber, although alternative example embodiments are not limited thereto.

The plastic material may include, but is not limited to, polymethyl methacrylate ("PMMA"), polytetrafluoroethylene ("PTFE"), polystyrene, polyethylene, and other materials. A crosslinked polymer may be used as the polymer to prevent a sample solution for detection from being impregnated with moisture, for example.

Further, the barriers 630 may have sufficient rigidity and density to not deform by mechanical waves generated from input IDTs 301.

A width of each of the barriers 630 may vary depending on an interval between the SAW unit sensors 310, 320 and 330, the properties of material used therefore, and/or for other considerations, and thus additional example embodiments are not limited to the foregoing description.

Referring now to FIGS. 12 and 13, yet another SAW sensor system 104 includes guiding layers 640 as the cutoffs between the SAW unit sensors 310, 320 and 330 and disposed on a base substrate 110.

The guiding layers 640 may be disposed on a portion where the SH SAW is generated or transmitted, such that the SH SAW is effectively prevented from being transmitted to the neighboring SAW unit sensors. In FIGS. 12 and 13, for example, each guiding layer 640 is formed in such a manner that it covers an entire upper, e.g., top, surface of each SAW unit sensor, from which a pad section of bar-type electrodes 303 of each SAW unit sensor is excluded, but alternative example embodiments are not limited to this configuration.

The guiding layers 640 are disposed on the respective SAW unit sensors 310, 320 and 330. Channels 641, having a predetermined width, are formed between the guiding layers 640. Thus, the guiding layers 640 are separately formed on the respective SAW unit sensors 310, 320 and 330, and a path of the SH SAW, which has an influence on each SAW unit sensor, is thereby interrupted.

The guiding layers 640 concentrate energy of the SAW on the respective SAW unit sensors 310, 320 and 330. Further, the guiding layers 640 effectively prevent the IDT electrodes 300 from coming into direct contact with a sample.

The guiding layers 640 may be independently formed on the respective SAW unit sensors 310, 320 and 330. In one or more additional example embodiments, the guiding layers 640 may be formed by applying a material to an entire surface of the piezoelectric substrate 200, and then removing the material from spaces between the SAW unit sensors 310, 320 and 330.

The guiding layers 640 may be formed of a sound wave absorbing material, as described in greater detail above with reference to the barriers 630. In additional example embodiments, however, the guiding layers 640 may be formed of silicon dioxide ($SiO_2$), polyimide or a combination or composite thereof.

In another example, the guiding layers 640 may be formed of acrylamide, purified agarose, N-vinyl pyrrolidone, methacrylate, N-isopropyl acrylamide, substituted acrylamide, or poly(ethylene glycol)diacrylate ("PEG-DA"). Alternatively, the guiding layers 640 may be formed of monomers or dimers including vinyl acetate, vinyl pyrrolidone, vinyl ether, olefin, styrene, vinyl chloride, ethylenes, acrylates, methacrylates, nitriles, acrylamides, maleates, epoxies, epoxides, lactones, ethylene oxides, ethylene glycols, ethyloazolines, amino acids, saccharides, proteins, anhydrides, amides, carbonates, phenylene oxides, acetals, sulfones, phenylene sulfides, esters, fluoropolymers, imides, amide-imides, etherimides, ionomers, aryletherketones, amines, phenols, acids, benzenes, cinnamates, azoles, silanes, chlorides, or polymers including N,N'-methylenebisacrylamide, methylenebismethacrylamide ethyleneglycol-dimethacrylate, polyethyleneglycol diacrylate ("PEGDA"), polyethyleneglycol dimethacrylate ("PEGDMA"), a polyvinylidene fluoride ("PVdF") based polymer, a polyacrylonitril ("PAN") based polymer, a polymethylmethacrylated ("PMMA") based polymer, a polyvinyl chloride ("PVC") based polymer, a mixture of the PVdF based polymer, PAN based polymer, PMMA based polymer, and PVC based polymer, and/or mixtures thereof.

Further, when a thickness of each guiding layer 640 is greater than a predetermined thickness, a frequency characteristic is changed by a mass effect. In contrast, when the thickness of each guiding layer 640 is less than the predetermined thickness, it is difficult to form the guiding layer 640, and thus a desired effect is not obtained. Accordingly, in one example embodiment, the thickness of each guiding layer 640 may be from about 0.1 micrometer (μm) to about 5 μm, and, in another example embodiment, may be from about 1 μm to about 3 μm, but alternative additional embodiments are not limited to the foregoing description and/or dimensions.

In addition to the structure described above with reference to FIGS. 1 to 14, a structure of the cutoff according to additional example embodiments is not limited, but instead may be constructed in any manner that interrupts and/or inhibits transmission of the SH SAW to the neighboring SAW unit sensors.

Figure 14:
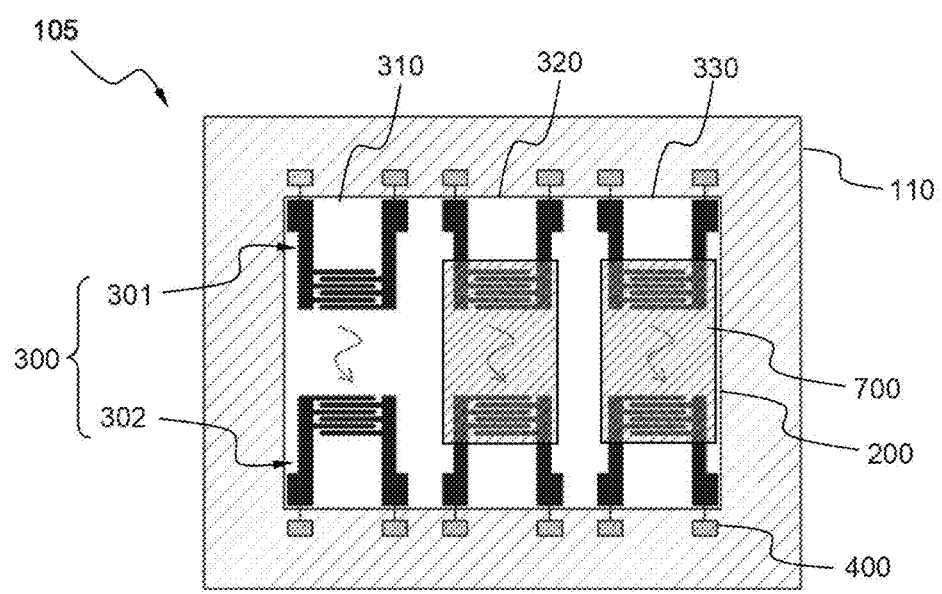
FIG. 14 is a plan view of a SAW sensor system according to still another example embodiment.

An operation of a SAW sensor system 105 according to one or more example embodiments will now be described in further detail with reference to FIG. 14, which is a plan view of a SAW sensor system according to still another example embodiment.

The SAW sensor system 105 includes three SAW unit sensors 310, 320 and 330 disposed on a base substrate 110. As described in greater detail above with reference to FIGS. 1 to 4, each of the SAW unit sensors 310, 320 and 330 includes a piezoelectric substrate 200 and an IDT electrode 300 having a pair of IDTs 301 and 302, e.g., an input IDT 301 and an output IDT 302, disposed on the piezoelectric substrate 200. The base substrate 110, the piezoelectric substrate 200, and the IDT electrode 300 have substantially the same configuration as those described in greater detail above with reference to FIGS. 1 to 4 and, accordingly, any repetitive detailed description thereof will hereinafter be simplified or omitted.

In the SAW sensor system 105, a reaction layer 700 is disposed on the second and third SAW unit sensors 320 and 330, but it is not formed on the first SAW unit sensor 310, for example.

Each reaction layer 700 is formed on the piezoelectric substrate 200 to cover the corresponding IDT electrode 300, and may be bonded to a detection target material or a receptor bonded to the detection target material. As a result, the first SAW unit sensor 310, on which the reaction layer 700 is not disposed, functions as a reference SAW unit sensor, and the second and third SAW unit sensors 320 and 330 function as reaction SAW unit sensors that react with a sample. A plurality of the reaction SAW unit sensors may be formed, based on a number of desired detection targets, and thus a he number of reaction SAW unit sensors is not limited to that shown or described herein.

Each reaction layer 700 includes a receptor that corresponds to a characteristic of the detection target material. For example, the receptors may include a gas adsorbent, an enzyme, a microorganism, an antibody and/or deoxyribonucleic acid (DNA), for example. The reaction layer 700 may have a shape of a layer or cell that immobilizes the receptors.

A driving principle of the second or third SAW unit sensor 320 or 330 will be now be described in further detail. An electrical signal produces a mechanical wave while passing through the IDT 301. This mechanical wave is changed by physical, chemical and/or electrical reactions, since the receptors and targets or bonding materials included in the reaction layer 700 of the surface of the SAW unit sensors 310, 320 and/or 330 are bonded to each other. Thus, a central frequency, phase or intensity, for example, of a signal outputted from the SAW unit sensors is changed. Specifically, for example, the target material is bonded to the reaction layer 700, and thus a mass of the reaction layer is changed. In this case, a shear speed of the SAW, vibrated by the input IDT 301, is changed. The output IDT 302, which receives this shear speed change, measures a change in an oscillation frequency, and the target material and/or its physical properties are thereby accurately detected. Furthermore, the target material may be analyzed qualitatively and quantitatively.

Thus, the signal change in the second or third SAW unit sensor 320 or 330 is observed in comparison with the signal of the first SAW unit sensor 310, so that example embodiments detect the target material bonded to the SAW unit sensors.

This SAW sensor system 105 analyzes physical properties of the target material such as mass, pressure, density and/or viscosity, for example. Further, the SAW sensor system 105 obtains a frequency change more accurately and precisely than in a conventional SAW sensor system, and my be applied to liquid and gas phases at the same time and, moreover, may have at least ten times the vibration frequency of a conventional biosensor. Thus, the SAW sensor system 105 according to the example embodiments described herein can be manufactured in a small size, due to easy integration, measure in real time, and reduce a required amount of sample to be measured. Thus, the SAW sensor system 105 may be applied to a biosensor, which is designed to detect physical properties and characteristics of a biological detection target material. As described herein, the biosensor is comprehensive of a measurement sensor using biological materials such as enzymes, microbes, and biological tissues, a measurement system sensor imitating the mechanism of a biological system, and a sensor performing measurement intended for the biological system, but is not limited thereto.

The detection target material may include biomolecules, such as proteins, antibodies, antigens, deoxyribonucleic acid ("DNA"), ribonucleic acid ("RNA"), bacteria, animal cells, viruses and/or tissues, for example, as well as biological solutions, such as toxins generated by the biomolecules, but is not limited thereto.

When the detection target material is the biological solution, the receptors uniquely bond to the detection target material and may include proteins, antigens, antibodies, DNA, RNA, peptide nucleic acid ("PNA," or "artificial DNA"), cells such as olfactory cells, and other materials.

For example, a presence of a predetermined disease may be detected using the SAW biosensor having a surface to which a receptor uniquely reacts with the disease is applied. Put another way, it can be determined whether a specimen, obtained from a patient, reacts with the receptor of the SAW biosensor. Accordingly, the SAW biosensor may be used to detect diseases. According to the example embodiments described herein, a variety of examinations may be rapidly performed using a small amount of sample, since a number of SAW unit sensors are provided in the SAW sensor system.

According to the example embodiment SAW sensor systems 100, 101, 102, 103, 104 and 105 described herein, SAW sensor systems are equipped with a plurality of SAW unit sensors, and it is thereby possible to reduce interference and noise of signal thereof. Further, the SAW sensor systems can be miniaturized through integration of the SAW unit sensors, and a required amount of a sample solution, including a detection target material such as a specimen of a patient, is substantially reduced. In addition, the SAW sensor systems can be applied to an oscillation mode, so that they have substantially improved sensitivity, as well as greatly improved economical and industrial utility values.

While the general inventive concept has been particularly shown and described herein with reference to example embodiments thereof, it will be understood by those of ordinary skill in the art that various changes in form and details may be made therein without departing from the spirit or scope of the present invention as defined by the following claims.

What is claimed is:

1. A surface acoustic wave sensor system, comprising:
a base substrate;
multiple surface acoustic wave unit sensors disposed on the base substrate, each surface acoustic wave unit sensor including an inter-digital transducer electrode including an input inter-digital transducer and an output inter-digital transducer paired with and facing the input inter-digital transducer, wherein the inter-digital transducer electrodes of the multiple surface acoustic wave unit sensors are mounted on a single piezoelectric substrate;
connection electrodes disposed in the base substrate and electrically connected to the surface acoustic wave unit sensors; and
cutoffs which prevent a shear horizontal surface acoustic wave from being transmitted between adjacent surface acoustic wave unit sensors, wherein the cutoffs comprise barrier walls disposed on the piezoelectric substrate between the surface acoustic wave unit sensors.

2. The surface acoustic wave sensor system according to claim 1, wherein the barrier walls comprise a sound wave absorbing material.

3. The surface acoustic wave sensor system according to claim 2, wherein the sound wave absorbing material is selected from a group consisting of plastics, waxes and silicon rubbers.

4. A surface acoustic wave sensor system, comprising:
a base substrate;
multiple surface acoustic wave unit sensors disposed on the base substrate, each surface acoustic wave unit sensor including an inter-digital transducer electrode including an input inter-digital transducer and an output inter-digital transducer paired with and facing the input inter-digital transducer, wherein
the input inter-digital transducers of the multiple surface acoustic wave unit sensors are commonly aligned in a first row,
the output inter-digital transducers of the multiple surface acoustic wave unit sensors are commonly aligned in a second row, and
the inter-digital transducer electrodes of the multiple surface acoustic wave unit sensors are mounted on a single piezoelectric substrate;
connection electrodes disposed in the base substrate and electrically connected to the surface acoustic wave unit sensors; and
cutoffs configured to prevent a shear horizontal surface acoustic wave from being transmitted between adjacent surface acoustic wave unit sensors.

5. The surface acoustic wave sensor system according to claim 4, wherein the cutoffs comprise grooves formed in the piezoelectric substrate and disposed between the surface acoustic wave unit sensors.

6. The surface acoustic wave sensor system according to claim 4, wherein the cutoffs comprise guiding layers formed by covering upper surfaces of the surface acoustic wave unit sensors.

7. The surface acoustic wave sensor system according to claim 6, wherein the guiding layers comprise a sound wave absorbing material.

8. The surface acoustic wave sensor system according to claim 7, wherein the guiding layers comprise a sound wave absorbing material.

9. The surface acoustic wave sensor system according to claim 6, wherein each guiding layer has a thickness from about 0.1 micrometer to about 5 micrometers.

10. The surface acoustic wave sensor system according to claim 4, wherein
at least one of the surface acoustic wave unit sensors is a reaction surface acoustic wave unit sensor on which a reaction layer is disposed, and
the reaction layer is disposed on the piezoelectric substrate to cover an inter-digital transducer electrode corresponding to the reaction surface acoustic wave unit sensor and includes a receptor which binds to a target material.

11. The surface acoustic wave sensor system according to claim 4, wherein at least one of the surface acoustic wave unit sensors is a reference surface acoustic wave unit sensor on which a reaction layer is not disposed.

12. The surface acoustic wave sensor system according to claim 4, wherein the surface acoustic wave sensor system analyzes at least two of mass, pressure, density and viscosity of a material by detecting a change in a signal outputted from the output inter-digital transducers.

13. The surface acoustic wave sensor system of claim 4, wherein the inter-digital transducer electrodes of the multiple surface acoustic wave sensors are disposed along a longitudinal direction on the piezoelectric substrate.

* * * * *